United States Patent
Chen et al.

(10) Patent No.: US 10,016,313 B2
(45) Date of Patent: Jul. 10, 2018

(54) METHOD FOR FOLDING ABSORBENT ARTICLES

(71) Applicant: The Procter & Gamble Company, Cincinnati, OH (US)

(72) Inventors: Ran Chen, Guangzhou (CN); Yize Fang, Hangzhou (CN)

(73) Assignee: The Procter & Gamble Company, Cincinnati, OH (US)

( * ) Notice: Subject to any disclaimer, the term of this patent is extended or adjusted under 35 U.S.C. 154(b) by 415 days.

(21) Appl. No.: 14/736,355

(22) Filed: Jun. 11, 2015

(65) Prior Publication Data

US 2015/0374555 A1   Dec. 31, 2015

(51) Int. Cl.
*A61F 13/15* (2006.01)
*B65H 45/04* (2006.01)

(52) U.S. Cl.
CPC ....... *A61F 13/15747* (2013.01); *B65H 45/04* (2013.01); *B65H 2301/312* (2013.01); *B65H 2301/342* (2013.01); *B65H 2404/2611* (2013.01); *B65H 2404/62* (2013.01); *B65H 2404/65* (2013.01); *B65H 2701/11234* (2013.01); *B65H 2701/1924* (2013.01); *B65H 2801/57* (2013.01)

(58) Field of Classification Search
None
See application file for complete search history.

(56) References Cited

U.S. PATENT DOCUMENTS

| | | |
|---|---|---|
| 5,540,647 A | 7/1996 | Weiermann |
| 5,989,175 A | 11/1999 | Kawanishi |
| 8,409,066 B2 | 4/2013 | Allen et al. |
| 2012/0157280 A1* | 6/2012 | Schneider ......... A61F 13/15747 493/374 |
| 2013/0052408 A1 | 2/2013 | Carlson |
| 2013/0244853 A1 | 9/2013 | Rosani et al. |

FOREIGN PATENT DOCUMENTS

| | | | |
|---|---|---|---|
| CN | 103662961 A | * | 3/2014 |
| EP | 0 171 486 B1 | | 6/1988 |
| JP | S58-13704 | | 1/1983 |
| JP | 04266360 A | * | 9/1992 ....... A61F 13/15747 |
| JP | H06115805 | | 4/1994 |
| JP | H0948405 A | | 2/1997 |
| JP | H107317 A | | 1/1998 |
| JP | 2001-008965 A | | 1/2001 |
| JP | 2003-267468 | | 9/2003 |
| JP | 2003267468 A | * | 9/2003 |
| JP | 4170567 B2 | | 10/2008 |
| JP | 2014-045847 A | | 3/2014 |
| WO | WO 1999-23984 A1 | | 5/1999 |

OTHER PUBLICATIONS

PCT International Search Report, not dated, dated Jul. 8, 2015 (6 pages).

* cited by examiner

*Primary Examiner* — Hemant M Desai
*Assistant Examiner* — Tanzim Imam
(74) *Attorney, Agent, or Firm* — George H. Leal; Andrew J. Mueller

(57) ABSTRACT

The present invention is related to a method for folding an article into three parts comprising first folding a leading end portion of the article to form a first folded article, and second folding a trailing end portion of the first folded article, wherein the first folded article is transported with a moving direction change no higher than about 45 degree.

7 Claims, 8 Drawing Sheets

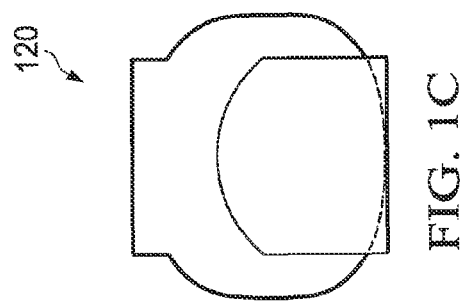
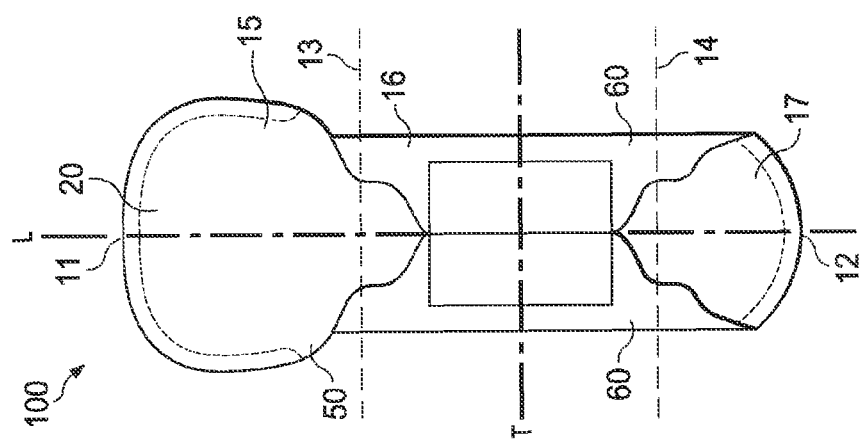
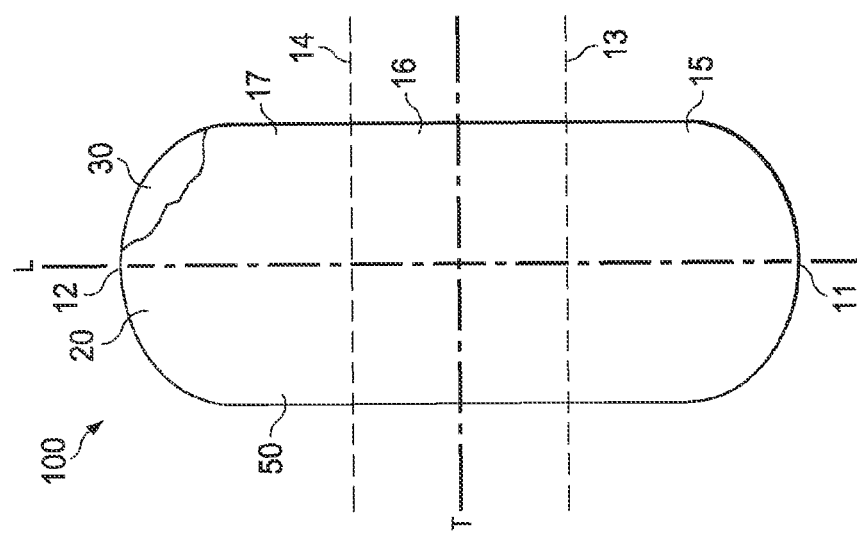

METHOD FOR FOLDING ABSORBENT ARTICLES

FIELD OF THE INVENTION

The present invention relates to methods for folding absorbent articles. Specifically, the method can be used to fold absorbent articles into three parts in a longitudinal direction.

BACKGROUND OF THE INVENTION

Absorbent articles such as sanitary napkins, adult incontinence articles, diapers and pantiliners are often manufactured and/or packaged on a high speed production line where individual articles may move along a production path at a speed of hundreds of meters per minute, for example higher than 200 m/min, and manufacturers of articles are continually trying to increase manufacturing speed.

During the manufacturing and/or packaging process, the absorbent article may undergo a folding process. One of ways to fold absorbent articles is a trifolding process by which an absorbent article is folded into three parts. A trifolding process may comprise folding absorbent articles about two fold lines which are transversal to their longitudinal axis, into three parts, respectively forming a leading portion, a central portion and a trailing portion of the article in a machine direction. In a trifolding process, an article may be first folded in around two thirds in the longitudinal direction by folding either the front portion or the rear portion, and second folded in around one third by folding the remaining rear portion or front portion. It is preferable that tri-folded pads has a consistent length among all the pads with minimum variation. However, current manufacturing practices often do not provide stable tri-folded product length for downstream pouch folding and packaging process, resulting in products that may have undesirable characteristics in the market place.

In a folding process providing a tri-folded article disclosed in Japanese laid-open patent publication No. 2002-18664, the folding process includes steps folding a trailing end portion first and then folding a leading end portion later. This type of process needs spacing between articles prior to first folding which requires accelerating moving speed of an article before the first folding. In addition, after tri-folding process, tri-folded product spacing needs to be reduced before moving into pouch folding process, which requires decelerating moving speed of an article. Such speed change tends to create increased article length variation which results in a wide variation in a tri-folded, article length which gets more conspicuous when process speed get faster.

In another folding process providing a tri-folded article disclosed in Japanese laid-open patent publication No. 2003/267468, the folding process includes steps of first folding a leading end portion, then turning the first folded article about 180 degree, and second folding a tailing end portion. This type of process may require a wide pad transition distance and product transition direction change between the first and the second folding steps which tends to increase article length variation. Product transition direction change between the first and second folding steps tends to increase article lenght variation. Japanese laid-open patent publication No. 2003/267468 discloses a folding equipment comprising a downward facing U-shape transport belt wrap around a guide drum which changes a moving direction of the first folded article about 180 degree.

Accordingly, there is a need for a process and a system for folding articles reducing tri-folded article length variation especially in high production speed.

In addition, there is a need for a process and a system for folding articles with minimizing an article transition distance and direction change between the first and second folding steps.

SUMMARY OF THE INVENTION

The present invention is directed to a method for folding an article into three parts comprising first folding a leading end portion of the article to form a first folded article, and second folding a trailing end portion of the first folded article, wherein the first folded article is transported with a moving direction change no higher than about 45 degree.

The present invention is also directed to an apparatus for folding an article into three parts comprising a) a first pathway comprising convey system transporting the article, b) a first fold means for folding a leading end portion of the article, c) a second pathway comprising convey system transporting the article, d) a second fold means for folding a trailing end portion of the article, e) a third pathway comprising convey system transporting the article, wherein the second pathway has an angle T of moving direction change of the article not higher than about 45 degree, and wherein the first pathway and the third pathway are placed in the same side of the second pathway.

BRIEF DESCRIPTION OF THE DRAWINGS

FIG. 1A is a plain view of an exemplary absorbent article.

FIG. 1B is a plain view of an absorbent article having flaps before tri-folding process.

FIG. 1C is a plain view of an exemplary tri-folded absorbent article.

DETAILED DESCRIPTION OF THE INVENTION

Definitions

Figure 2:
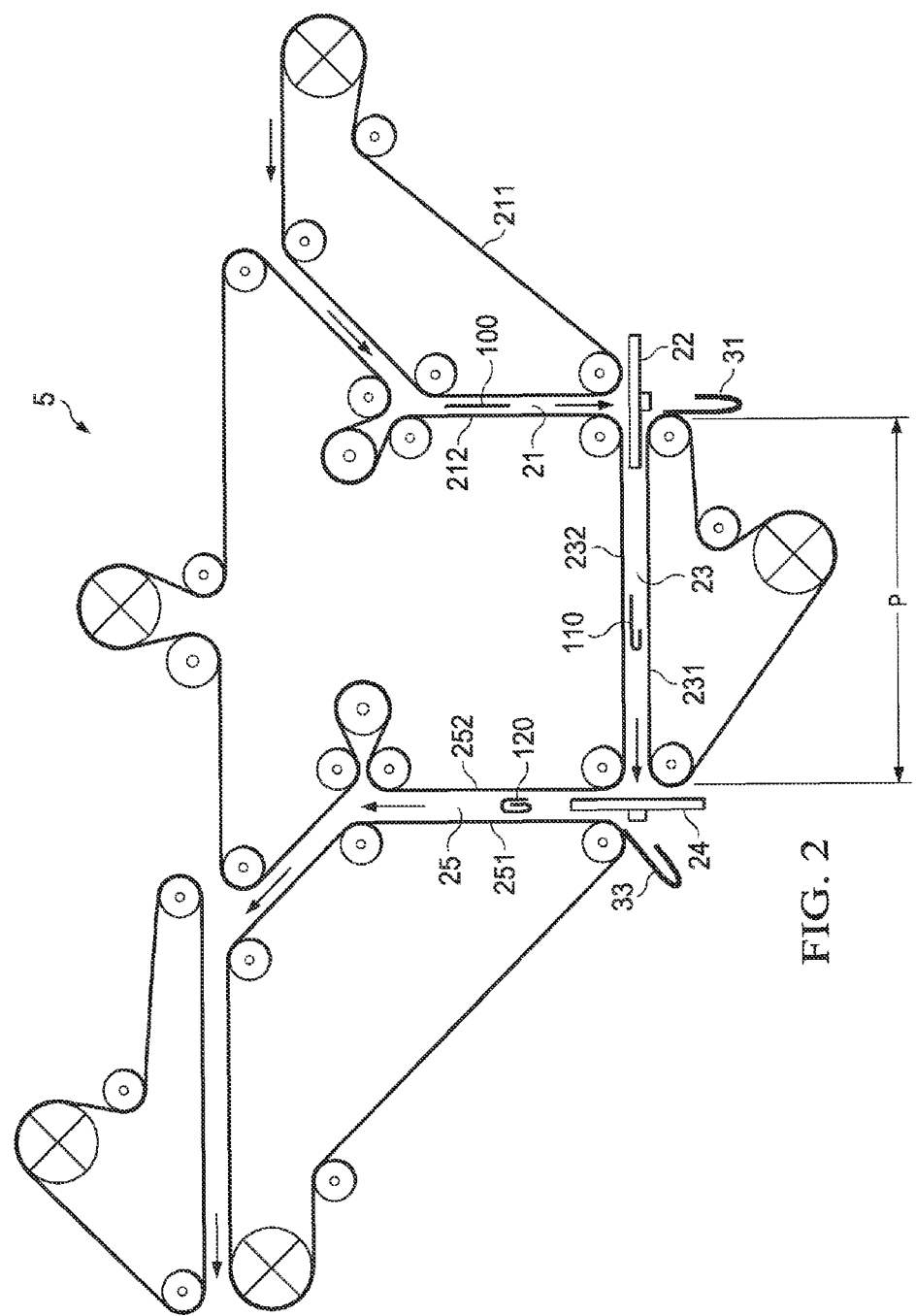
FIG. 2 is a side view of a schematic representation of a folding apparatus in accordance with an embodiment of the present invention.

The term "absorbent article", as used herein, includes disposable articles such as sanitary napkins, panty liners, diapers, adult incontinence articles, and the like. Such absorbent articles are intended for the absorption of body liquids, such as menses or blood, vaginal discharges, urine, and feces. Various absorbent articles described above will typically comprise a liquid permeable topsheet, a liquid impermeable backsheet joined to the topsheet, and an optional absorbent core between the topsheet and backsheet.

The term "body facing surface", as used herein, refers to the side of the absorbent article facing the body of the user when in use, while the term "garment facing surface" as used herein refers to the outer or exterior surface of any article component that is intended to be worn or positioned adjacent a wearer's undergarments, or in the case of an absorbent article which is not worn by the user, the garment surface is typically positioned adjacent a user's hand or other implement assisting in the use of the absorbent article.

The term "comprising", as used herein and in the claims, is inclusive or open-ended and does not exclude additional unrecited elements, compositional components, or method steps.

The term "engage," as used herein, refers to the context of transferring an article from one pathway to another or from a portion of one pathway to another portion of the same pathway, means coming into close proximity (e.g., <10 cm, up to and including physical contact) such that an engaging force (e.g., suction) present at the surface of a carrier of the pathway can be applied to an article.

As used herein, a "fold line" is the portion of an article about which the article is folded. The fold line typically extends from one side edge to the opposing side edge in the crotch regions and, at least one of the leading portion edge and the trailing portion edge of an article may be aligned with one of fold lines when the article is folded.

The term "leading end portion", as used herein, refers to a portion of an article that is forward of the first fold line in machine direction while the term "trailing end portion" refers to a portion of an article that is after the second fold line in the machine direction, and "central portion" refers to a portion connecting the leading end portion and the end trailing portion. The leading end portion and the trailing end portion do not necessarily means a front side portion and a rear side portion of an article respectively in terms of wearer's usage purposes.

The term "machine direction" or "MD", as used herein, refers to the path that material, such as a web, follows through a manufacturing process, while the term "cross machine direction" or "CD" is the direction substantially perpendicular to the MD. Directions within 45 degrees of the cross direction are considered to be cross directional.

The term "trifold" or "trifolded", as used herein, means folding an article having a leading end portion, a central portion, a trailing end portion, a first surface and a second surface opposite to the first surface into three portions. For example, trifolding an absorbent article may be accomplished by folding a leading end portion toward the first surface of a central portion of the article, and folding a trailing end portion toward the second surface of the leading end portion to cover at least a part of the second surface of the leading end portion as the article moves in the machine direction of travel, such that the article is folded along fold lines into three portions. In another example, trifolding an absorbent article may be accomplished by folding a leading end portion toward the first surface of a central portion of the article, and folding a trailing end portion toward the second surface of the leading end portion but not to cover the second surface of the leading end portion as the article moves in the machine direction of travel, such that the article is folded along fold lines into three portions.

For ease of understanding, portions of the following description may be exemplified in terms of an absorbent article. However, it is to be understood that while one or more particular examples recited herein may refer to a sanitary napkin, the present invention is not limited to such articles. The folding and transfer system described herein may, in fact, be practiced in any situation where an article exhibiting the characteristics described herein is required. Examples of other articles include hard surface cleaning wipes or pads; pre-moistened cloths; paper towels; dryer sheets and dry-cleaning clothes; adult incontinence briefs and undergarments; diapers; feminine hygiene garments such as panty liners, absorbent inserts, and the like; toilet paper; tissue paper; personal cleaning wipes or clothes such as baby wipes or facial wipes; packaging components and substrates and/or containers for laundry detergent and coffee, which may be produced in pellets or pouches and may be manufactured in a converting or web process; or even discrete products produced at high speed such as high-speed bottling lines, cosmetics, razor blade cartridges, and disposable consumer batteries.

Regarding all numerical ranges disclosed herein, it should be understood that every maximum numerical limitation given throughout this specification includes every lower numerical limitation, as if such lower numerical limitations were expressly written herein. In addition, every minimum numerical limitation given throughout this specification will include every higher numerical limitation, as if such higher numerical limitations were expressly written herein. Further, every numerical range given throughout this specification will include every narrower numerical range that falls within such broader numerical range and will also encompass each individual number within the numerical range, as if such narrower numerical ranges and individual numbers were all expressly written herein.

Absorbent Article

Absorbent articles folded by a method according to the present invention comprise a liquid pervious topsheet, a liquid impervious backsheet joined to the topsheet, and optionally an absorbent core located between the topsheet and the backsheet. The absorbent articles of the present invention may have a pair of flaps on longitudinal sides of a body-facing surface for folding around and securing the absorbent article to an undergarment.

FIG. 1A shows a plain view of an exemplary absorbent article 100. The article 100 includes a body-faceable, liquid pervious topsheet 20, and a garment-faceable, liquid impervious backsheet 30 joined with the topsheet 20. The article 100 also includes a longitudinal centerline L, a transversal centerline T, a leading edge 11, a trailing edge 12, a first fold line 13 positioned between the leading edge 11 and the transversal line T and parallel to the transversal line T, and a second fold line 14 positioned between the trailing edge 12 and the transversal line T and parallel to the transversal line T.

An absorbent article may have a pair of flaps 60 on longitudinal sides of a body-facing surface for folding around and securing the absorbent article to the undergarment. When the absorbent article has a pair of flaps, the flaps are folded toward a longitudinal centerline of the article before a first folding according to the present invention as shown in FIG. 1B.

According to the methods and apparatuses disclosed herein, the article 100 may have fold lines dividing the absorbent article into three portions in the machine direction of travel, and be folded first about the first fold line 13 such that the leading end portion 15 and the center portion 16 are positioned in a face-to-face relationship along a body facing surface 50, and then folded about the second fold line 14 such that the body facing surface 50 of the trailing end portion 17 is positioned onto a garment facing area of the leading end portion 15.

A folded absorbent article according to certain embodiments may have the leading edge 11 and the second fold line 14 aligned and/or the trailing edge 12 and the first fold line 13 aligned.

In another example, according to the methods and apparatuses disclosed herein, the article 100 may have fold lines dividing the absorbent article into three portions in the machine direction of travel in a way that not all the three portions are in equal length, and be folded first about the first fold line 13 such that the leading end portion 15 and part of the center portion 16 are positioned in a face-to-face relationship along a body facing surface 50, and then folded about the second fold line 14 such that the trailing end portion 17 and part of the center portion 16 are positioned in a face-to-face relationship along a body facing surface 50.

A folded absorbent article produced according to the present invention preferably have a trifold configuration having an average MD length accuracy of ±6 mm, and an average CD width accuracy of ±3 mm when measured by a ruler.

FIG. 1C shows a plain view of a tri-folded article 120.
Folding Process and Apparatus FIG. 2 shows a side view of an exemplary folding apparatus 5 according to the present invention for transferring and folding an article such as the article 100 shown and described in FIG. 1A and FIG. 1B. As illustrated in FIG. 2, selective folding apparatus 5 may include a first pathway 21 for transporting an article 100, a second pathway 23 for transporting a first folded article 110, a third pathway 25 for transporting a second folded absorbent article 120, a first fold means 22 for folding the article 100 and delivering the first folded article 110 to the second pathway 23, and a second fold means 24 for folding the first folded article 110 and delivering the second folded article 120 to the third pathway 25. In some embodiments, the folding apparatus 5 may further include a defect sensor 24, for detecting cut web products 20 that contain at least one defect or otherwise do not meet satisfactory conditions. In a further embodiment, when the article 100 has a pair of flaps, the folding apparatus 5 may include a folding device for folding the flaps of the articles 100 and delivering the article 100 to the first pathway 21.

As illustrated in FIG. 2, in an embodiment, articles 100 are delivered to a first pathway 21, first folded articles 110 are delivered to a second pathway 23, and second folded articles 120 are delivered to a third pathway 25. Articles 100, first folded articles 110, and second folded articles 120 travel along the first pathway 21, the second pathway 23 and the third pathway 25, respectively, by means of a conveyor system. In an embodiment, the conveyor system comprises a belt and roller system. In other embodiments, the conveyor system may comprise any other suitable mechanism, including but not limited to, a conveyor or transport drum, for causing articles 100, first folded articles 110 and second folded article 120 to travel along the first pathway 21, the second pathway 23, the third pathway 25, respectively. In an embodiment, the first pathway 21 comprises an outer conveyor belt 211 on which one surface of the article 100 is placed and an inner conveyor belt 212 disposed facing the other surface of the article 100. The first pathway 21 transports the article 100 toward first fold means 22 located near the end edge of the first pathway 21.

Figure 3:
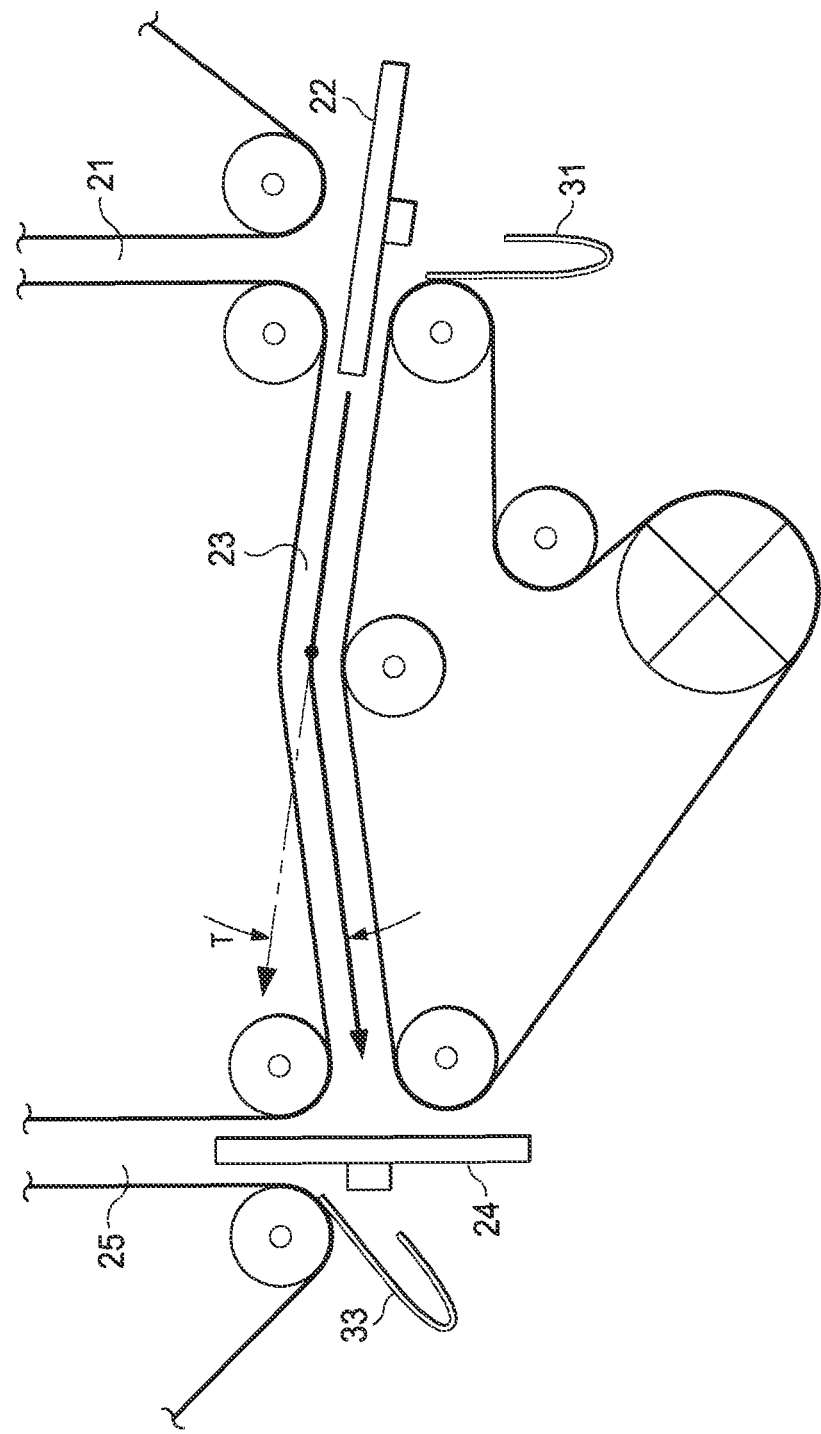
FIG. 3 is a side view of a schematic representation of a second pathway of a folding apparatus in accordance with another embodiment of the present invention.

A second pathway 23 may comprises outer conveyor belt 231 on which one surface of first folded article 110 is placed and inner conveyor belt 232 disposed facing the other surface of the first folded article 110. The second pathway 23 transports the first folded article 110 toward second fold means 24 located near the end edge of the second pathway 23. The second pathway 23 may be substantially linear, bent or curved. When it is bent or curved, as shown in FIG. 3, an angle T of moving direction change of the first folded article 110 is not higher than about 45 degree. A second pathway 23 may be bent upwards as shown in FIG. 3, or be bent downwards. A folded product length variation may become bigger when angle T increase, as this may impact the first folded article 110 transition in the second pathway 23 and thus the folding means cannot not consistently hit the same position in articles, and cause MD length variation in articles. If this angle is higher than 45 degree, a first folded article 110 may tend to stretch around this turning point. This stretching force may impact the article transition smoothness and create increased MD length variation which causes defects in folded articles and packaging quality. The second pathway 23 is preferably substantially linear.

A length P of the second pathway 23 is preferably no longer than about 3 meters, more preferably no longer than about 2 meters, even more preferably no longer than about 3 times a length of an article. If the length P of the second pathway 23 especially in a high speed process is too long, a length variation in MD in the article 100 tends to be bigger. In addition, if P of the second pathway 23 is longer than about 3 meters, convey belt tension and CD tracking may be difficult to control and conveyor belt slip and CD tracking deviation may be amplified, which will cause defects in folded products and packaging quality defect. A length P of the second pathway 23 is preferably not shorter than the same as a length of the article 100. If the length P is too short, an article is second folded before a first folding of an article is completed which may create an unstable positioning of an article during article transition.

The length P of about 1.5-about 3 times length of article 100 is preferably. When the second pathway 23 is not continuous and consists of multiple conveyor systems comprising a conveyor belt and roller system, a length P of the second pathway 23 is understood a total of a length of each conveyor belt and a space between two consecutive conveyor belts.

When the second pathway 23 is not continuous and consists of multiple conveyor systems comprising a conveyor belt and roller system, a length P of the second pathway 23 is understood a total of a length of each conveyor belt and space between two consecutive conveyor belts.

As illustrated in FIG. 2, third pathway 25 may comprise an outer conveyor belt 251 on which one surface of second folded articles 120 are placed and an inner conveyor belt 252 disposed facing the other surface of the second folded articles 120. The third pathway 25 transports the second folded articles 120.

In one embodiment, the inner conveyor belts 212, 232 and 252 are connected and continuous. In one embodiment, the first pathway 21 and the third pathway 25 are disposed in the same side about the second pathway 23 as shown in FIGS. 2 and 3.

First fold means 22 is located in a finishing end side of the first pathway in a machine direction and second fold means 24 is located in a finishing end side of the second pathway in a machine direction. First fold means 22 is located between the first pathway 21 and the second pathway 23, so that when the leading end portion of the article 100 projects from the end edge of the first pathway 21, the first fold means 22 folds the article 100 along a first fold line and further causes the first folded article 110 to be delivered to the second pathway 23.

Second fold means 24 is located between the second pathway 23 and the third pathway 25, so that when the first folded article 110 projects from the end edge of the second pathway 23, the second fold means 24 folds the first folded article 110 delivered from the second pathway 23 along a second fold line and further causes the second folded article 120 to be delivered to the third pathway 25.

In further embodiments, the second folded articles 120 may travel along another pathway or be subjected to further processing, such as wrapping, stacking, packaging, etc.

The process according to the present invention can reduce folded pad length variation, avoid skewed folding, prevent tri-folded article 120 in crimp attribute defect, stabilize following transition process between article fabrication machines and a packaging machine, and enhancing bag tightness and appearance.

Figure 4A:
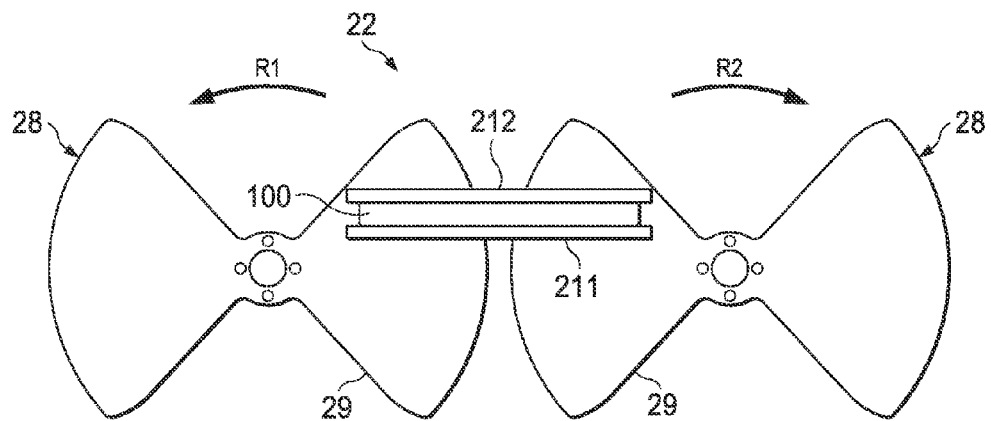
FIG. 4A is a front view of a folding mechanism of a selective first folding apparatus in accordance with an embodiment of the present invention.

Fold means suitable for the folding apparatus in accordance with the present invention may be a pair of tuckers rotating in opposite directions. In an embodiment of a folding apparatus 5 as shown in FIG. 4A, the first fold means 22 may be dual propeller-style tuckers 28 which rotate in opposite directions indicated by rotational arrows R1 and R2, each propeller type tucker having two blades 29 each. In other embodiments, a fewer or greater number of blades 29 may be provided on each propeller type tucker 28. For example, a propeller type tucker 28 may comprise a single blade or may comprise three or more blades. In yet other embodiments, it is recognized that a single propeller type tucker 28 may be provided instead of a pair of propeller type tuckers 28. It is recognized further that any suitable number of propeller type tuckers 28, each with any suitable number of blades, may be provided. The blades may be provided in any desired shape or configuration.

Figure 4B:
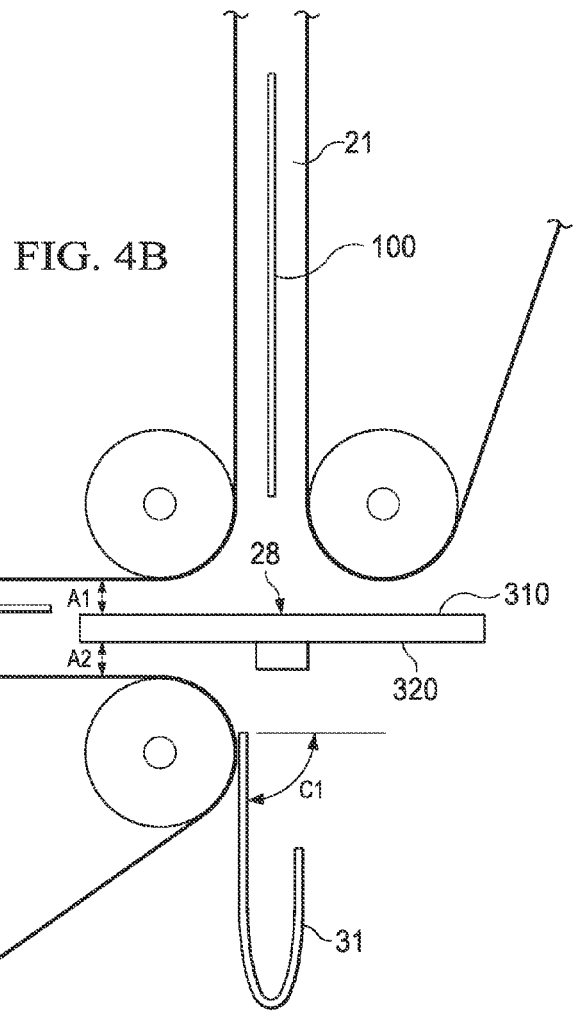
FIG. 4B is a side view of a folding mechanism of a selective first folding apparatus in accordance with an embodiment of the present invention of FIG. 4A.

As can be seen in FIG. 4B showing a side view of first folding mechanism with a the propeller-style tuckers 28 shown in FIG. 4A, the propeller-style tuckers 28 may be phased such that blades 29 engage the article 100 as the article 100 travels along the first pathway 21 and pass by the fold means, a propeller type tucker 28 in this case. In a first folding in the process in accordance with the present invention, blades 29 may engage the article 100 substantially at a first fold line, thereby folding the article 100 substantially two thirds of initial length of the article 100. However, it is recognized that the first fold line may in a position other than substantially one third of the length of the article 100, and thus the article 110 is folded other than substantially two thirds of initial length of the article depending on product designs. A pair of propeller style tuckers 28 further directs the first folded article 110 to the second pathway 23.

"Clearance A1" refers to the shortest distance between a surface of the inner conveyor belt 232 of the second pathway 23 towards the outer conveyor belt 231 and a top surface 310 of a blade of the first tucker when the blade is engaged with the article 100. A1 may be in the range of from about 50% to about 150% of a thickness of the article 100. "Clearance A2" refers to the shortest distance between a surface of the outer conveyor belt 231 of the second pathway 23 towards the inner conveyor belt 232 and a bottom surface 320 of a blade of the first tucker when the blade is engaged with the article 100. A2 may be in the range of from about 20% to about 150% of a thickness of the article 100. Clearance A1 and A2 in a preferable range may avoid tearing of a topsheet and crimp attribute defect of an absorbent article, and secure consistent length of tri-folded articles.

Figure 4C:
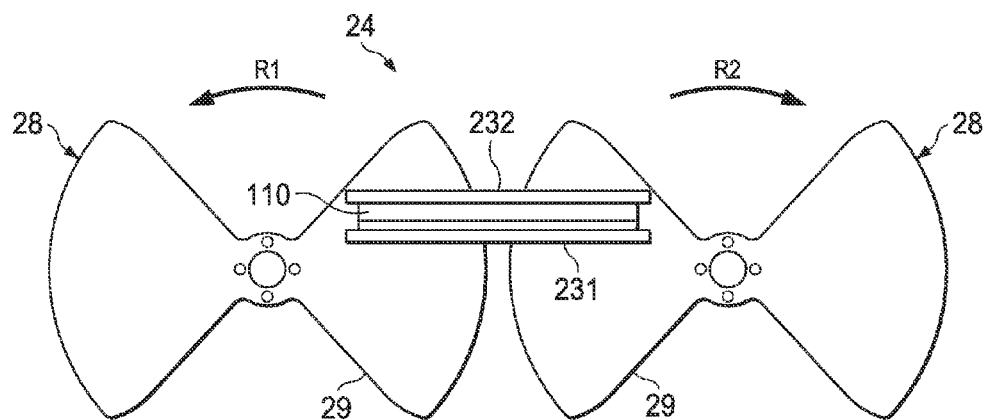
FIG. 4C is a front view of a folding mechanism of a selective second folding apparatus in accordance with an embodiment of the present invention.
Figure 4D:
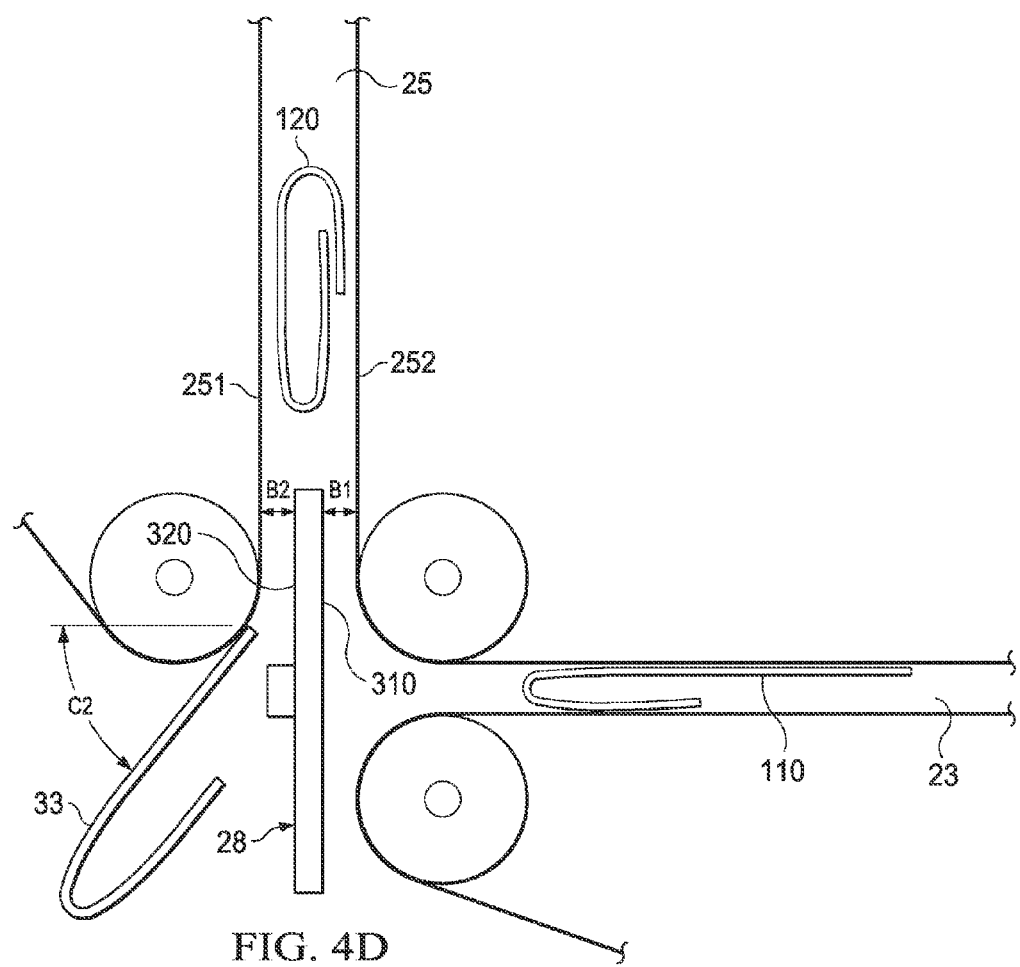
FIG. 4D is a side view of a folding mechanism of a selective second fold apparatus in accordance with an embodiment of the present invention of FIG. 4C.

As can be seen in FIGS. 4C and 4D showing folding mechanism of an exemplary second folding apparatus having a second folding means 24, a dual propeller-style tuckers 28 rotates in opposite directions, each propeller type tucker having two blades 29 each. propeller type tuckers 28 may be phased such that blades 29 engage first folded article 110 as the first folded article 110 travels along first pathway 23 and pass by fold means, propeller type tuckers 28 in this case. In a second folding in the process in accordance with the present invention, blades 29 may engage the first folded article 110 substantially at a second fold line, thereby folding the first folded article 110 substantially one third of initial length of the article 100. However, it is recognized that tucker blades 29 may engage first folded articles 110 in a position other than substantially at the second fold line of articles 100 depending on product designs. A pair of propeller style tuckers 28 further directs the second folded article 120 to third pathway 25. "Clearance B1" refers to the shortest distance between a surface of the inner conveyor belt 252 of the third pathway 25 towards the inner conveyor belt 252 a top surface 310 of a blade of the tucker when the blade is engaged with the first folded article 110, and may be in the range of from about 50% to about 150% of a thickness of the article 100. "Clearance B2" refers to the shortest distance between a surface of the outer conveyor belt 251 of the third pathway 25 towards the inner conveyor belt 252 and a bottom surface 320 of a blade of the tucker when the blade is engaged with the first folded article 110, and may be in the range of from about 20% to about 150% of a thickness of the article 100. Clearance B1 and B2 in a preferable range may avoid tearing of a topsheet and crimp attribute defect of an absorbent article, and secure consistent length of tri-folded articles.

Other suitable forms of fold means also may be appropriate for use with some embodiments of selective fold means of the present disclosure. It is further recognized that the terms tucker, or tucker blade may refer to any suitable mechanism for engaging the articles 100 or the first folded article 110 and causing the articles 100 or the first folded article 110 to be folded about a folding line—typically, though not exclusively, an imaginary line—that defines two or more generally symmetrical or asymmetrical portions the articles 100 or the first folded article 110. Furthermore, tucker blades 29 may be manufactured from any suitable materials such as, but not limited to, metal, metallic alloys, plastics, etc., or combinations thereof.

As shown in FIGS. 4B and 4D, the apparatus in accordance with the present invention may further comprise a holder. A first holder 31 may avoid article 100 to be girded by second pathway 23 before first fold means 22. The first holder 31 may be positioned to have a tucker holder angle C1, an angle between a line parallel to the outer conveyor belt 231 of the second pathway 23 and the first holder 31, in the range of from about 20 degree to about 120 degree. A second holder 33 may direct the first folded article 110 to change transition direction before second fold means 24 and avoid the first folded article 110 reopen during the second folding process. The second holder 33 may be positioned to have a tucker holder angle C2, an angle between a line parallel to the inner conveyor belt 232 of the second pathway 23 and the second holder 33, in the range of from about 20 degree to about 80 degree.

Figure 5A:
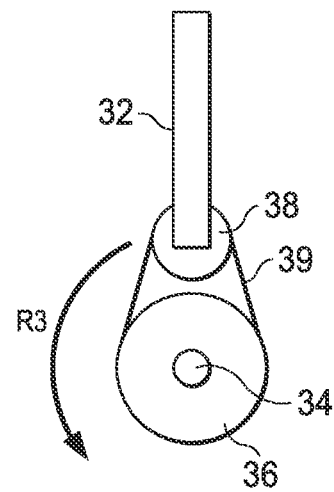
FIG. 5A is a front view of another folding mechanism means of a folding apparatus in accordance with an embodiment of the present invention.

FIG. 5A illustrates a further embodiment of fold means suitable for the present invention. Fold means may include tucker blade 32, shaft 34, fixed gear 36, rotating gear 38, and drive belt 39. Rotating gear 38 may orbit fixed gear 36, as shown by rotational arrow R3. In a further embodiment, fixed gear 36 and drive belt 39 may cause rotating gear 38 to rotate around its central axis. One end of tucker blade 32 may be fixed at substantially near the central axis of rotating gear 38, thereby causing tucker blade 32 to rotate with rotating gear 38. Other suitable means may be used for obtaining substantially the same effect and rotation of tucker blade 32, including, for example, replacing drive belt 40 with at least one gear or gearbox. It is further recognized that more than one rotating gear 38 and tucker blade 32 may be provided to orbit fixed gear 36.

Figure 5B:
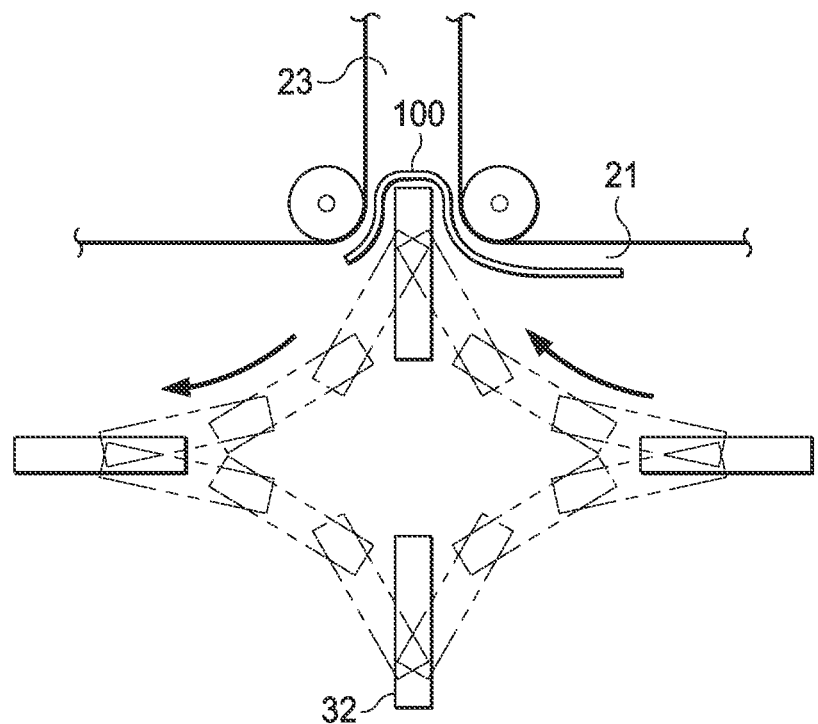
FIG. 5B is a side view of a folding mechanism means of a folding apparatus in accordance with an embodiment of the present invention of FIG. 5A.

FIG. 5B illustrates a path that may be followed by tucker blade 32 in an embodiment of fold means illustrated in FIG. 5A when used as a first fold means. The dashed-line tucker blades represent positions that tucker blade 32 may be located at some time throughout the orbit and rotation of rotating gear 38. For ease of illustration, embodiments of shaft 34, fixed gear 36, rotating gear 38, and drive belt 39 have been removed from FIG. 5B. As can be seen in FIG. 5B, fold means may be phased such that tucker blade 32 engages an article 100 as the article 100 travels along the first pathway 21 and pass by the fold means. The tucker blade 32 may engage the article 100 for folding at a predetermined position. For example, the tucker blade 32 may engage the article 100 in a position substantially one third of the length of the article. For example, the tucker blade 32 may engage the article 100 in a position other than substantially one third of the length of the article. Tucker blade 32 may further direct a folded article to a next pathway. The fold mean shown in FIG. 5A may be used as a second fold mean with the same mechanism explained above.

Figure 6A:
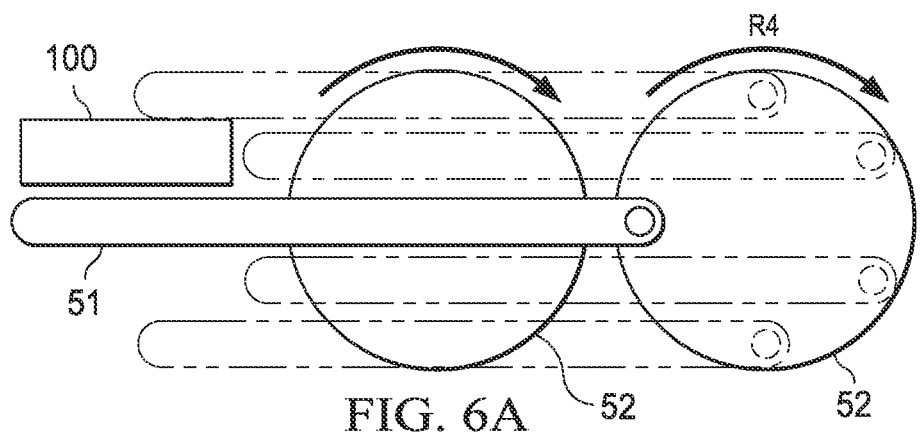
FIG. 6A is a front view of another folding mechanism means of a folding apparatus in accordance with an embodiment of the present invention.
Figure 6B:
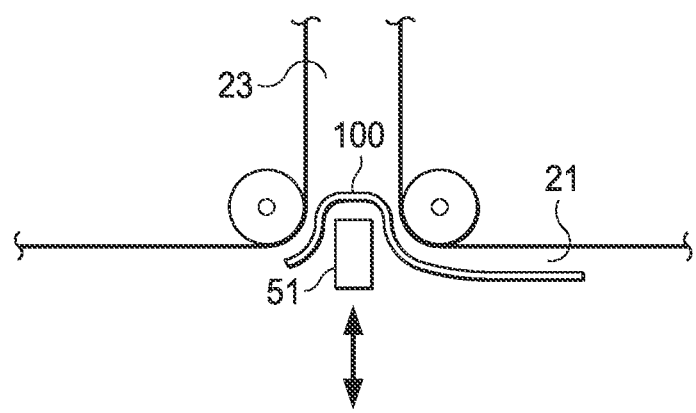
FIG. 6B is a side view of a folding mechanism means of a folding apparatus in accordance with an embodiment of the present invention of FIG. 6A.

Yet another embodiment of fold means for the present invention can be seen in FIG. 6A. Fold means may include tucker arm 51 and rotating arm 52. Tucker arm 51 may be attached at one end to rotating arm 52. Rotating arm 52 may rotate in place around a central axis of rotating arm 52, such as is illustrated by rotational arrow R4. In some embodiments, fold means may include more than one rotating arm 52, as shown in FIG. 6A. In further embodiments, rotating arm 52 may be a rotating bar, rotating plate, or rotating planetary gear system, or any other suitable structure or configuration. It is recognized that any means for rotating may be used for, or in place of, rotating arm 52. As rotating arm 52 rotates, tucker arm 51 may follow the path shown by the dashed-line tucker arms in FIG. 6A. The dashed-line tucker arms represent positions that tucker arm 51 may be located at some time throughout the orbit and rotation of rotating arm 52. As can be seen in FIG. 6A, as tucker arm 51 rotates with rotating arm 52, it may maintain a configuration wherein at any position during rotation, tucker arm 51 may be substantially parallel to any other position during rotation of tucker arm 51. As can be seen in FIG. 6B, when the fold means is used as the first fold means, the fold means may be phased such that tucker arm 51 engages article 100 as the article 100 travels along first pathway 21 and pass by fold means. Tucker arm 51 may engage article for folding at a predetermined position.

Other suitable forms of fold means also may be appropriate for use with some embodiments of selective folding apparatus of the present disclosure. It is further recognized that the terms tucker, tucker blade, or tucker arm may refer to any suitable mechanism for engaging an article and causing the article to be folded about an axis—typically, though not exclusively, an imaginary line—that defines two or more generally symmetrical or asymmetrical portions of the article. Furthermore, tucker blades 29 and 32 and tucker arm 51 may be manufactured from any suitable materials such as, but not limited to, metal, metallic alloys, plastics, etc., or combinations thereof.

Figure 7:
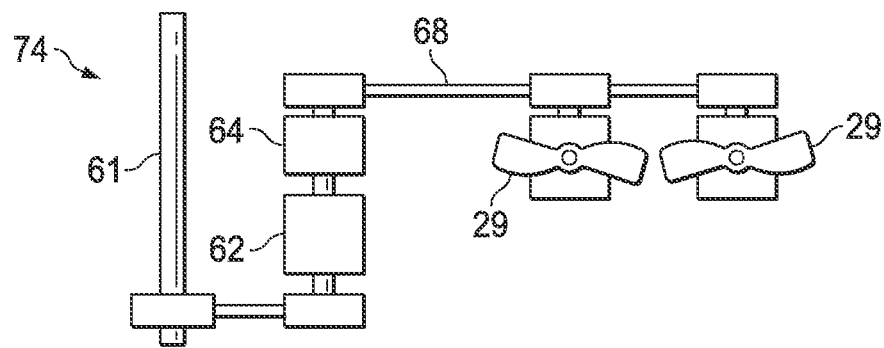
FIG. 7 is a front view of a drive mechanism of a folding mechanism of a selective folding apparatus in accordance with another embodiment of the present disclosure.

Fold means may comprise any drive mechanism 74 for operating a tucker blade. In an embodiment of fold means, illustrated in FIG. 7, drive mechanism 74 may be a line shaft drive mechanism comprising main shaft 61, phasing gear box 62, disengagement clutch 64, and linking belt 68. Not all components of the line shaft drive mechanism shown in FIG. 7 are required, and some components may be eliminated from the line shaft drive mechanism without departing from the scope of the present disclosure, while others may be added or substituted.

In an embodiment, main shaft 61 may directly drive the fold means. In a further embodiment, main shaft 61 may indirectly drive the fold means. For example, in an embodiment, the main shaft 61 may be linked to phasing gear box 62, which may phase the driving rotation of main shaft 61 to engage fold means with passing an article. A line shaft drive mechanism may further include disengagement clutch 64. Disengagement clutch 64 may cause fold means to slow down, stop, and/or restart during operation of a folding apparatus. That is, at any suitable moment, disengagement clutch 64 may cause drive mechanism 74 to slow down or stop, which may further prevent fold means from engaging, folding, and/or delivering an article. In other embodiments, disengagement clutch 64 may be replaced by other suitable mechanisms for slowing or stopping fold means from engaging or folding an article, or delivering an article to a next pathway. Linking belt 68 may link main shaft 61, phasing gear box 62, or disengagement clutch 64 with tucker blades 29 or 32 or tucker arm 51. In an embodiment, linking belt 68 may be a belt or chain. In alternative embodiments, linking belt 68 may be any suitable means for connecting main shaft 61, phasing gear box 62, or disengagement clutch 64 with tucker blades 29 or 32 or tucker arm 51, such that drive mechanism 74 is linked to tucker blades 29 or 32 or tucker arm 51, such as via gears or gearboxes.

Figure 8:
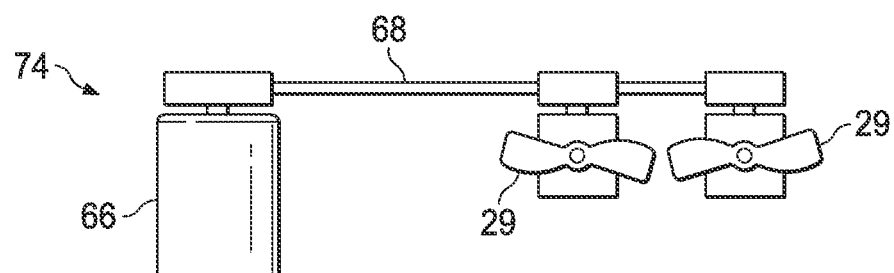
FIG. 8 is a front view of a drive mechanism of a folding mechanism of a selective folding apparatus in accordance with yet another embodiment of the present disclosure.

In another embodiment, illustrated in FIG. 8, drive mechanism 74 may include motor 66 and linking belt 68. Motor 66, in a further embodiment, may be a servo motor for controlling the position of tucker blades 29 or 32 or tucker arm 51 of fold means. A servo motor may be used to alter the speed of fold means quickly, including accelerating, decelerating, stopping, and restarting fold means in a very short period of time. For example, a servo motor may be used to accelerate, decelerate, stop, and restart fold means, including in a relatively short period of time, such as seconds or fractions of a second, such as milliseconds. In other embodiments a servo motor may be used to accelerate, decelerate, stop, and restart fold means in any interval of time. Linking belt 68 may link motor 66 with tucker blades 29 or 32 or tucker arm 51. As previously stated, linking belt 68 may be a belt or chain. In alternative embodiments, linking belt 68 may be any suitable means for linking motor 66 with tucker blades 29 or 32 or tucker arm 51, such that drive mechanism 74 is linked to tucker blades 29 or 32 or tucker arm 51, such as via gears or gearboxes.

Figure 9:
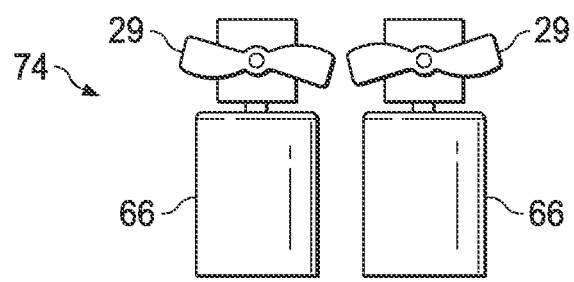
FIG. 9 is a front view of a drive mechanism of a folding mechanism of a selective folding apparatus in accordance with a further embodiment of the present disclosure.

In yet a further embodiment, shown in FIG. 9, linking belt 68 may be eliminated from drive mechanism 74. Motor 66, such as a servo motor, may be linked directly to tucker blades 29 or 32 or tucker arm 51, such that the motor 66 directly controls tucker blades 29 or 32 or tucker arm 51. Drive mechanism 74, illustrated in FIG. 9, may provide even less driven inertia and lower momentum forces during slowing or stopping of fold means and may allow even faster conveyor speeds and higher precision of fold means than the mechanisms in FIG. 7 or 8.

Although fold means illustrated in FIGS. 7-9 includes dual propeller-style tuckers, it is recognized that any tucker blade, or any other suitable structure, may be used in accordance with fold means of the present disclosure. For example, fold means may comprise any tucker blade system described above in combination with any drive mechanism 74 described above. Alternatively, fold means may comprise any suitable tucker blade system in combination with any suitable drive mechanism.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for folding an article along a transversal first fold line and a transversal second fold line of the article, the article having a leading end portion, a trailing end portion, and a central portion connecting the leading end portion and the trailing end portion in a longitudinal direction, the method comprising:
    a) transporting the article to a first fold means by a first pathway comprising a first convery system,
    b) folding the leading end portion of the article transported by the first pathway along the first fold line to form a first folded article and delivering the first folded article to a second pathway comprising a second convey system by the first fold means,
    c) transporting the first folded article to a second fold means by the second pathway,
    d) folding the trailing end portion of the first folded article along the second fold line to form a second folded article and delivering the second folded article to a third pathway comprising a third convey system by the second fold means, and
    e) transporting the second folded article by the third pathway, wherein the first fold means is located in a finishing end side of the first pathway in a machine direction and the second fold means is located in a finishing end side of the second pathway in the machine direction, wherein the first folded article is transported with an angle of moving direction change no higher than 45 degrees, wherein the second pathway has a length that and the article has a length, and wherein the length of the second length is greater than or equal to the length of the article but no longer than 3 meters.

2. The method for folding an article according to claim 1, wherein the second pathway is linear.

3. The method for folding an article according to claim 1, wherein at least one of the first fold means and the second fold means is a folding means having a tucker blade.

4. The method for folding an article according to claim 3, wherein the folding means is a dual propeller-style tucker.

5. The method for folding an article according to claim 1, wherein the first fold line and the second fold line divide the article into three portions in the machine direction.

6. The method for folding an article according to claim 1, wherein the first fold line and the second fold line divide the article into three portions in a way that at least two of the three portions have different lengths in the machine direction.

7. The method for folding an article according to claim 1, wherein the article is an absorbent article.

* * * * *